United States Patent
Nix et al.

(10) Patent No.: US 9,938,588 B2
(45) Date of Patent: Apr. 10, 2018

(54) **COMPOSITIONS AND METHODS FOR DETECTING *ENTEROVIRUS* D68**

(71) Applicant: The United States of America, as represented by the Secretary, Dept. of Health and Human Services, Washington, DC (US)

(72) Inventors: William Allan Nix, Bethlehem, GA (US); M. Steven Oberste, Johns Creek, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/173,450

(22) Filed: Jun. 3, 2016

(65) Prior Publication Data
US 2016/0355897 A1 Dec. 8, 2016

Related U.S. Application Data

(60) Provisional application No. 62/171,657, filed on Jun. 5, 2015.

(51) Int. Cl.
| | | |
|---|---|---|
| *C12Q 1/70* | (2006.01) |
| *A61K 39/12* | (2006.01) |
| *A61K 39/00* | (2006.01) |
| *C12N 7/00* | (2006.01) |
| *C07K 14/005* | (2006.01) |
| *C12Q 1/68* | (2006.01) |
| *G01N 33/569* | (2006.01) |

(52) U.S. Cl.
CPC .................................. *C12Q 1/701* (2013.01)

(58) Field of Classification Search
CPC ............... A61K 2300/00; A61K 39/12; A61K 2039/6075; C12N 7/00; C12N 2770/32311; C12N 2770/32351; C07K 14/005; C12Q 1/70; C12Q 1/6806; G01N 33/56983
See application file for complete search history.

(56) References Cited

U.S. PATENT DOCUMENTS

| | | | | |
|---|---|---|---|---|
| 7,247,457 | B2 * | 7/2007 | Nix ........................ | C12Q 1/701 435/5 |
| 7,435,539 | B2 | 10/2008 | Oberste et al. | |
| 7,563,577 | B2 | 7/2009 | Paul, III et al. | |
| 7,714,122 | B2 * | 5/2010 | Nix ........................ | C12Q 1/701 536/24.3 |
| 2006/0003352 | A1 | 1/2006 | Lipkin et al. | |
| 2007/0287148 | A1 * | 12/2007 | Nix ........................ | C12Q 1/701 435/5 |
| 2011/0097704 | A1 | 4/2011 | Sampath et al. | |
| 2016/0312314 | A1 * | 10/2016 | Storch .................. | C12Q 1/6806 |

FOREIGN PATENT DOCUMENTS

| | | |
|---|---|---|
| WO | WO 98/14611 | 4/1998 |
| WO | WO 99/53097 | 10/1999 |

OTHER PUBLICATIONS

Marras Sae. Chapter 1: Selection of Fluorophore and Quencher Pairs for Fluorescent Nucleic Acid Hybridization Probes. From: Methods in Molecular Biology: Fluorescent Energy Transfer Nucleic Acid Probes: Designs and Protocols. Edited by: V.V. Didenko © Humana Press Inc., Totowa, NJ. Aug. 3, 2006.*
TaqMan® Copy Number Assays Protocol. Applied Biosystems by Life Technologies Corporation. Sep. 2010. https://tools.thermofisher.com/content/sfs/manuals/cms_062368.pdf.*
Brown et al., "Seven Strains of Enterovirus D68 Detected in the United States during the 2014 Severe Respiratory Disease Outbreak," *Genome Announcements*, vol. 2, No. 6, e01201-14, 2014 (1 page).
Centers for Disease Control and Prevention, "Enterovirus D68 (EV-D68) 2014 Outbreak Strain-Specific Real-Time Reverse Transcription/Polymerase Chain Reaction (rRT-PCR) Assay Instructions—Version Oct. 14, 2014," PDF file obtained from http://www.cdc.gov/non-polio-enterovirus/hcp/EV-D68-hcp.html, Oct. 14, 2014 (13 pages).
Centers for Disease Control and Prevention, "Enterovirus D68 for Health Care Professionals," http://www.cdc.gov/non-polio-enterovirus/hcp/EV-D68-hcp.html, downloaded Dec. 1, 2014 (3 pages).
Centers for Disease Control and Prevention, "Enterovirus D68 2014 Real-Time RT-PCR Assay," http://www.fda.gov/downloads/MedicalDevices/Safety/EmergencySituations/UCM446784.pdf, May 12, 2015 (31 pages).
Genbank Accession No. KM851225.1, Oct. 10, 2014 (4 pages).
Imamura et al., "Enterovirus 68 among Children with Severe Acute Respiratory Infection, the Philippines," *Emerging Infectious Diseases*, vol. 17, No. 8, pp. 1430-1435, 2011.
Kodani et al., "Application of TaqMan Low-Density Arrays for Simultaneous Detection of Multiple Respiratory Pathogens," *Journal of Clinical Microbiology*, vol. 49, No. 6, pp. 2175-2182, 2011.
Nijhuis et al., "Rapid and Sensitive Routine Detection of All Members of the Genus *Enterovirus* in Different Clinical Specimens by Real-Time PCR," *Journal of Clinical Microbiology*, vol. 40, No. 10, pp. 3666-3670, 2002.

(Continued)

*Primary Examiner* — Rachel B Gill
(74) *Attorney, Agent, or Firm* — Klarquist Sparkman, LLP

(57) ABSTRACT

Methods and compositions for detection of *enterovirus* D in a sample, particularly detection of *enterovirus* D68, are provided. The methods include contacting a sample with at least one primer (such as a forward primer and/or a reverse primer) capable of specifically amplifying an EV-D68 viral protein 1 (VP1) nucleic acid or a portion thereof and/or a detectably labeled probe capable of specifically hybridizing to an EV-D68 VP1 nucleic acid, under conditions sufficient for specific amplification of the EV-D68 VP1 nucleic acid by the at least one primer and/or under conditions sufficient for specific hybridization of the probe to the EV-D68 nucleic acid. The amplification of the EV-D68 VP1 nucleic acid and/or the hybridization of the probe to the EV-D68 VP1 nucleic acid is detected, thereby identifying presence of EV-D68 in the sample.

14 Claims, 3 Drawing Sheets

(56) References Cited

OTHER PUBLICATIONS

Nix et al., "Sensitive, Seminested PCR Amplification of VP1 Sequences for Direct Identification of All Enterovirus Serotypes from Original Clinical Specimens," *Journal of Clinical Microbiology*, vol. 44, No. 8, pp. 2698-2704, 2006.

Noordhoek et al. "Clinical validation of a new real-time PCR assay for detection of enteroviruses and parechoviruses, and implications for diagnostic procedures," *Journal of Clinical Virology*, vol. 41, pp. 75-80, 2008.

Oberste et al., "Comparative evaluation of Taqman real-time PCR and semi-nested VP1 PCR for detection of enteroviruses in clinical specimens," *Journal of Clinical Virology*, vol. 49, pp. 73-74, 2010.

Oberste et al., "Enterovirus 68 is associated with respiratory illness and shares biological features with both the enteroviruses and the rhinoviruses," *Journal of General Virology*, vol. 85, pp. 2577-2584, 2004.

Oberste et al., "Species-specific RT-PCR amplification of human enteroviruses: a tool for rapid species identification of uncharacterized enteroviruses," *Journal of General Virology*, vol. 87, pp. 119-128, 2006.

Selvaraju et al., "Optimization of a Combined Human Parechovirus-Enterovirus Real-Time Reverse Transcription-PCR Assay and Evaluation of a New Parechovirus 3-Specific Assay for Cerebrospinal Fluid Specimen Testing," *Journal of Clinical Microbiology*, vol. 51, No. 2, pp. 452-458, 2013.

Verstrepen et al., "Rapid Detection of Enterovirus RNA in Cerebrospinal Fluid Specimens with a Novel Single-Tube Real-Time Reverse Transcription-PCR Assay," *Journal of Clinical Microbiology*, vol. 39, No. 11, pp. 4093-4096, 2001.

Wylie et al., "Development and Evaluation of an Enterovirus D68 Real-Time Reverse Transcriptase PCR Assay," *J. Clin. Microbiol.*, vol. 53, No. 8, pp. 2641-2647, 2015.

Zhang et al., "A One-Step, Triplex, Real-Time RT-PCR Assay for the Simultaneous Detection of Enterovirus 71, Coxsackie A16 and Pan-Enterovirus in a Single Tube," *PLOS One*, 9(7):e102724, 2014 (6 pages).

\* cited by examiner

FIG. 3

GTATTATTACCACTACCATTCACTGCTAC (SEQ ID NO: 8)
GTATTATTACTACCATTCACNGCNAC (SEQ ID NO: 2)
GTGCTGTTGTTGCTACC---TACTGCCAC (SEQ ID NO: 9)

COMPOSITIONS AND METHODS FOR DETECTING *ENTEROVIRUS* D68

CROSS REFERENCE TO RELATED APPLICATION

This claims the benefit of U.S. Provisional Application No. 62/171,657, filed Jun. 5, 2015, which is incorporated herein by reference in its entirety.

FIELD

This disclosure relates to compositions and methods for detecting *enterovirus* (EV) in a sample, particularly EV-D68.

BACKGROUND

*Enterovirus* D68 (EV-D68; genus *Enterovirus*, family Picornaviridae) can cause severe respiratory illness, with clinical manifestations that include bronchiolitis, wheezing, and pneumonia, especially in children (Schieble et al., *Am. J. Epidemiol.* 85:297-310, 1967). Since its discovery in 1962, EV-D68 had been relatively rare until it re-emerged in the mid-2000s; since then it has been associated with clusters and outbreaks of severe respiratory disease worldwide (Ikeda et al., *Microbiol. Immunol.* 56:139-143, 2012; Imamura et al., *Emerg. Infect. Dis.* 17:1430-1435, 2011; Kaida et al., *Emerg. Infect. Dis.* 17:1494-1497, 2011; Linsuwanon et al., *PLoS One* 12:e35190, 2012; Jacobson et al., *Pediatr. Infect. Dis. J.* 42:309-312, 2012; Rahamat-Langendoen et al., *J. Clin. Virol.* 52:103-106, 2011; Tokarz et al., *J. Gen. Virol.* 93:1952-1958, 2012; Renois et al., *J. Clin. Microbiol.* 51:640-643, 2013; Todd et al., *Virol. J.* 10:103, 2013; Xiang et al., *Emerg. Infect. Dis.* 18:821-814, 2012). Beginning in August 2014, EV-D68 caused an ongoing outbreak of severe lower respiratory tract illness among children in the United States, with over 800 laboratory-confirmed cases in 46 states and the District of Columbia (Midgely et al., *MMWR* 63:798-799, 2014)

SUMMARY

Disclosed herein are methods and compositions for detection of *enterovirus* D in a sample, particularly detection of *enterovirus* D68 (EV-D68). In some embodiments, disclosed herein are methods for detecting EV-D68 in a sample (such as a sample from a subject infected with or suspected to be infected with EV-D68). In particular embodiments, the disclosed methods specifically detect EV-D68 (for example, 2014 North America lineages of EV-D68 virus).

The methods include contacting a sample with at least one primer (such as a forward primer and/or a reverse primer) capable of specifically amplifying an EV-D68 viral protein 1 (VP1) nucleic acid and/or a detectably labeled probe capable of specifically hybridizing to an EV-D68 VP1 nucleic acid under conditions sufficient for specific amplification of the EV-D68 VP1 nucleic acid by the at least one primer and/or under conditions sufficient for specific hybridization of the probe to the EV-D68 nucleic acid. The amplification of the EV-D68 VP1 nucleic acid and/or the hybridization of the probe to the EV-D68 VP1 nucleic acid is detected, thereby identifying presence of EV-D68 in the sample.

In particular embodiments, the methods include contacting the sample with a forward primer and a reverse primer capable of specifically amplifying an EV-D68 VP1 nucleic acid (such as SEQ ID NO: 4) or a portion thereof, and contacting the sample with a detectably labeled probe capable of specifically hybridizing to an EV-D68 VP1 nucleic acid (such as SEQ ID NO: 4) under conditions sufficient for amplification of the EV-D68 VP1 nucleic acid and hybridization of the probe to the EV-D68 VP1 nucleic acid. The amplification of the EV-D68 VP1 nucleic acid and/or hybridization of the probe to the EV-D68 VP1 nucleic acid is then detected. In some examples, the disclosed methods include carrying out real-time PCR or real-time reverse transcription-PCR (rRT-PCR). In some examples, the primers include a nucleic acid sequence with at least 90% sequence identity to SEQ ID NOs: 1 and 2. In other examples, the probe includes a nucleic acid sequence with at least 90% sequence identity to SEQ ID NO: 3.

Also disclosed herein are isolated primers and probes (such as detectably labeled probes), for example SEQ ID NOs: 1-3, for detection of EV-D68 VP1 nucleic acids and kits including one or more of the disclosed primers and/or probes.

The foregoing and other features of the disclosure will become more apparent from the following detailed description, which proceeds with reference to the accompanying figures.

BRIEF DESCRIPTION OF THE DRAWINGS

FIG. 3 is a sequence alignment of the EV-D68 reverse primer sequence (SEQ ID NO: 2) with corresponding sequences from a major cluster EV-D68 2014 North America lineage virus (GenBank Accession No. KM851225) and an EV-D68 virus from an earlier circulating EV-D68 virus (GenBank Accession No. KM851231). The earlier lineage virus sequence (SEQ ID NO: 9) has a three nucleotide deletion compared to the 2014 North America lineage virus sequence (SEQ ID NO: 8) and the reverse primer sequence (SEQ ID NO: 2).

SEQUENCE LISTING

Any nucleic acid and amino acid sequences listed herein or in the accompanying sequence listing are shown using standard letter abbreviations for nucleotide bases and amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on May 18, 2016, and is 3443 bytes, which is incorporated by reference herein.

SEQ ID NO: 1 is the nucleic acid sequence of an exemplary EV-D68 VP1 forward primer.

SEQ ID NO: 2 is the nucleic acid sequence of an exemplary EV-D68 VP1 reverse primer.

SEQ ID NO: 3 is the nucleic acid sequence of an exemplary EV-D68 VP1 probe.

SEQ ID NO: 4 is an exemplary EV-D68 VP1 encoding nucleic acid.

SEQ ID NOs: 5-7 are amino acid sequences corresponding to SEQ ID NOs: 1-3, respectively.

SEQ ID NOs: 8 and 9 are nucleic acid sequences of the reverse primer region of KM851225 and KM851231, respectively.

DETAILED DESCRIPTION

I. Abbreviations

EV *enterovirus*
EV-D68 *enterovirus* D68
rRT-PCR real-time reverse transcription-polymerase chain reaction
RV rhinovirus
snPCR semi-nested PCR
VP1 viral protein 1

II. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics,* 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as they were present in GenBank on May 15, 2015. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of this disclosure, the following explanations of specific terms are provided:

Amplification: Increasing the number of copies of a nucleic acid molecule, such as a gene or fragment of a gene, for example at least a portion of an EV-D68 nucleic acid molecule. The products of an amplification reaction are called amplification products. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include real-time PCR, reverse transcription PCR (RT-PCR), real-time RT-PCR (rRT-PCR), loop-mediated isothermal amplification (LAMP; see Notomi et al., *Nucl. Acids Res.* 28:e63, 2000); reverse-transcription LAMP (RT-LAMP); strand displacement amplification (see U.S. Pat. No. 5,744,311); transcription-mediated amplification (U.S. Pat. No. 5,399,491) transcription-free isothermal amplification (see U.S. Pat. No. 6,033,881); repair chain reaction amplification (see International Pat. Publ. No. WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Conditions sufficient for: Any environment that permits the desired activity, for example, that permits specific binding or hybridization between two nucleic acid molecules and/or that permits amplification of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), and so on).

Contact: Placement in direct physical association; for example in solid and/or liquid form. For example, contacting can occur in vitro with one or more primers and/or probes and a biological sample (such as a sample including nucleic acids) in solution.

Detectable label: A compound or composition that is conjugated directly or indirectly to another molecule (such as a nucleic acid molecule) to facilitate detection of that molecule. In some examples, a detectable label is covalently attached to a nucleic acid molecule, for example to a nucleotide present in a nucleic acid molecule or to the sugar-phosphate backbone of a nucleic acid molecule. Specific, non-limiting examples of labels include fluorescent and fluorogenic moieties (e.g., fluorophores), chemiluminescent moieties, chromogenic moieties, haptens (such as biotin, digoxigenin, or fluorescein), affinity tags, and radioactive isotopes (such as $^{32}P$, $^{33}P$, $^{35}S$, and $^{125}I$). The label can be directly detectable (e.g., optically detectable) or indirectly detectable (for example, via interaction with one or more additional molecules that are in turn detectable).

Methods for labeling nucleic acids, and guidance in the choice of labels useful for various purposes, are discussed, e.g., in Green and Sambrook, *Molecular Cloning: A Laboratory Manual,* 4th Ed., Cold Spring Harbor Laboratory Press (2012) and Ausubel et al., *Current Protocols in Molecular Biology,* John Wiley & Sons (1995, and including updates).

Figure 1:
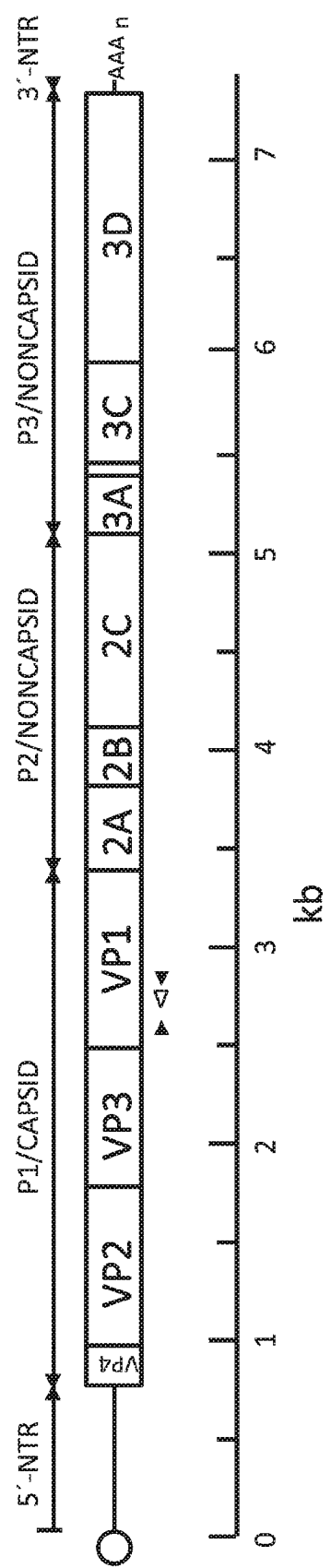
FIG. 1 is a schematic diagram of the *enterovirus* genome showing the location of the primers and probe used in the EV-D68 rRT-PCR assay disclosed herein (diagram not to scale). The filled triangles represent forward (right-facing) and reverse (left-facing) primers. The open triangle represents the probe.

*Enterovirus*: A genus of positive-strand RNA viruses. *Enteroviruses* have a genome of about 7500 nucleotides encoding an about 2200 amino acid polyprotein processed into four structural (capsid) proteins (VP1-VP4) and seven non-structural proteins (NS2A-2C and NS3A-3D). The *enterovirus* genome also includes a 5' non-translated region (5' NTR), which includes an internal ribosome entry site and initiation of positive-strand RNA synthesis, and a 3' NTR, which includes initiation of negative-strand RNA synthesis. See, e.g., FIG. 1.

*Enteroviruses* were originally classified according to biological (disease) properties as polioviruses, Coxsackie A viruses, Coxsackie B viruses, echoviruses, and *enteroviruses*. The current classification groups the viruses using molecular and biological properties as species *Enterovirus* (EV) A-J and Rhinovirus (RV) A-C. Each species includes multiple serotypes. Polioviruses are classified as EV-C. The Coxsackieviruses are a non-phylogenetic group classified under three *enterovirus* species (EV-A, EV-B, and EV-C). The echoviruses (E-1 to E-33) are classified under EV-B, and the remaining *enteroviruses* are found among EV-A to EV-J.

*Enterovirus* D68 (EV-D68): EV-D68 is a serotype of EV-D that was originally identified in California in 1962 (Schieble et al., *Am. J. Epidemiol.* 85:297-310, 1967). This virus can cause mild to severe respiratory illness, with clinical manifestations including fever, runny nose, sneezing, cough, and body aches in mild cases and bronchiolitis, wheezing, and pneumonia in more severe cases.

Nucleic acid and protein sequences for EV-D68 are publicly available. For example, GenBank Accession Nos. KM851225 through KM851230 disclose exemplary EV-D68 genomic nucleic acid sequences, all of which are incorporated by reference as present in GenBank on May 15, 2015.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes and/or primers disclosed herein (for example, as a detectable label covalently attached to a probe or primer) are known to those of skill in the art and include 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxyfluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CalRed 590, CalRed 610, CalRed615, CalRed 635, CalGreen 520, CalGold 540, and CalOrange 560 (Biosearch Technologies, Novato, Calif.). One skilled in the art can select additional fluorophores, for example those available from Thermo-Fisher Scientific (Waltham, Mass.).

In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a quencher, such as Dabcyl, QSY7 (Molecular Probes), QSY33 (Molecular Probes), BLACK HOLE QUENCHERS™ (Biosearch Technologies; such as BHQ0, BHQ1, BHQ2, and BHQ3), ECLIPSE™ Dark Quencher (Epoch Biosciences), or IOWA BLACK™ (Integrated DNA Technologies). A quencher can reduce or quench the emission of a donor fluorophore.

"Donor Fluorophores" are fluorophores or luminescent molecules capable of transferring energy to an acceptor fluorophore, in some examples generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Isolated: An "isolated" biological component (such as a nucleic acid) has been substantially separated or purified away from other biological components that are present (for example, in a sample or in which the component naturally occurs), such as other chromosomal and extrachromosomal DNA, RNA, and proteins. Nucleic acids that have been "isolated" include nucleic acids purified by standard purification methods. The term also includes nucleic acids prepared by recombinant expression in a host cell, as well as chemically synthesized nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Primer: Primers are short isolated nucleic acids, generally DNA oligonucleotides 10 nucleotides or more in length (such as 10-60, 15-50, 20-45, or 20-40 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by PCR, real-time PCR, real-time RT-PCR, or other nucleic acid amplification methods known in the art.

Probe: A probe typically comprises an isolated nucleic acid (for example, at least 10 or more nucleotides in length) with an attached detectable label or reporter molecule. Typical labels include radioactive isotopes, ligands, chemiluminescent agents, fluorophores, and enzymes. Methods for labeling oligonucleotides and guidance in the choice of labels appropriate for various purposes are discussed, e.g., in Green and Sambrook (2012) and Ausubel et al. (1995).

Sample: A specimen (such as a biological or environmental specimen) containing DNA (for example, genomic DNA or cDNA), RNA (including mRNA), protein, or combinations thereof. Examples include, but are not limited to isolated nucleic acids, cells, cell lysates, chromosomal preparations, peripheral blood, serum, plasma, urine, saliva, respiratory samples (such as nasopharyngeal, oropharyngeal, or bronchoalveolar lavage samples), tissue biopsies (such as a tumor biopsy or lymph node biopsy), surgical specimens, bone marrow, amniocentesis samples, and autopsy material. In one example, a sample includes viral nucleic acids, for example, EV-D68 RNA or DNA reverse transcribed from EV-D68 RNA. In particular examples, samples are used directly (e.g., fresh or frozen), or can be manipulated prior to use, for example, by lysis and/or nucleic acid isolation or purification.

Specific amplification or specific hybridization: Amplification of and/or hybridization to substantially or preferentially only a defined target nucleic acid or class of target nucleic acid. In an example, a probe "specifically hybridizing to an EV-D68 VP1 nucleic acid" is capable of specifically hybridizing to a VP1 nucleic acid from an EV-D68 virus, but not a VP1 nucleic acid from an EV-A, EV-B, EV-C, RV-A, RV-B, EV-D70, EV-D94, EV-D111, or EV-D120 virus. In another example, a primer "capable of specifically amplifying an EV-D68 VP1 nucleic acid" is capable of specifically amplifying a VP1 nucleic acid from an EV-D68 virus, but not a VP1 nucleic acid from an EV-A, EV-B, EV-C, RV-A, RV-B, EV-D70, EV-D94, EV-D111, or EV-D120 virus. In particular examples, a probe "specifically hybridizing to an EV-D68 VP1 nucleic acid" or a primer "capable of specifically amplifying an EV-D68 VP1 nucleic acid" is capable of specifically hybridizing to or amplifying a VP1 nucleic acid from a 2014 EV-D68 North America lineage but not a VP1 nucleic acid from EV-D68 Fermon strain.

Subject: Any multi-cellular vertebrate organism, such as human and non-human mammals (including non-human primates). In one example, a subject is known to be or is suspected of being infected with an *enterovirus*, such as EV-D68.

Viral Protein 1 (VP1): One of four structural proteins that form the *enterovirus* capsid. The *enterovirus* capsid is formed from viral protein 1 (VP1), viral protein 2 (VP2), viral protein 3 (VP3), and viral protein 4 (VP4).

Nucleotide and amino acid sequences of EV-D68 VP1 are publicly available. In one example, a nucleic acid sequence encoding an EV-D68 VP1 polypeptide includes:

```
                                          (SEQ ID NO: 4)
CTAGACCATTTACATGCAGCAGAGGCAGCCTACCAGATCGAGAGCATCAT

CAAAACAGCGACCGACACTGTGAAAAGTGAGATTAATGCTGAACTTGGTG

TGGTCCCTAGCTTAAATGCAGTTGAAACAGGTGCAACTTCTAACACTGAA

CCAGAAGAAGCCATACAAACTCGCACAGTGATAAATCAGCACGGTGTATC

CGAGACTCTAGTGGAGAATTTTCTCAGTAGAGCAGCTTTGGTATCAAAGA

GAAGTTTTGAATACAAAGATCATACTTCGTCTACAGCACGAGCAGACAAG

AACTTTTTCAAATGGACAATTAACACCAGATCCTTTGTACAGTTAAGAAG

AAAATTAGAATTATTCACATACCTTAGATTTGATGCTGAGATCACTATAC

TCACAACTGTAGCAGTGAATGGTAGTGGTAATAATACATACGTGGGTCTT

CCTGACTTGACACTTCAAGCAATGTTTGTACCCACTGGTGCTCTTACCCA

GAAAAGCAGGACTCATTCCACTGGCAGTCAGGCAGTAATGCTAGTGTATT

CTTTAAAATCTCCGACCCCCCAGCCAGAATAACCATACCTTTTATGTGCA

TTAACTCAGCATACTCAGTTTTTTATGATGGCTTTGCCGGATTTGAGAAA

AACGGTCTGTATGGAATAAATCCAGCTGACACTATTGGTAACTTATGTGT

TAGAATAGTGAATGAACACCAACCAGTTGGTTTCACAGTGACCGTTAGGG

TTTACATGAAGCCTAAACACATAAAAGCATGGGCACCACGACCACCACGA

ACTCTGCCATATATGAGTATTGCAAATGCAAATTACAAAGGTAAAGAAAG

AGCACCAAATGCGCTCAGTGCTATAATTGGCAATAGAGACAGTGTCAAAA

CCATGCCTCATAATATAGTGAACACT
```

Additional exemplary EV-D68 VP1 nucleic acid sequences include GenBank Accession Nos. KP745754 (nucleotides 2341-3267, EV-D68 isolate NY130), KP745753 (nucleotides 2305-3231, EV-D68 isolate NY126), KP745757 (nucleotides 2354-3280, EV-D68 isolate NY210), KP114662 (nucleotides 2169-3095, EV-D68 isolate EV68 Alberta17390_2014), KP322752 (nucleotides 2292-3218, EV-D68 strain US/CA/14-6089), and KP100793 (nucleotides 2355-3281, EV-D68 strain US/CO/14-94), all of which are incorporated by reference herein as present in GenBank on May 15, 2015. One of ordinary skill in the art can identify additional EV-D68 VP1 nucleotide sequences and corresponding VP1 amino acid sequences.

III. Methods of Detecting EV-D68

Methods for detecting the presence of EV-D68 in a sample are disclosed, for example, utilizing the primers and/or probes disclosed herein. The methods described herein may be used for any purpose for which detection of EV-D68 is desirable, including diagnostic and prognostic applications, such as in laboratory and clinical settings.

In some embodiments, the disclosed methods include amplifying from a sample an EV-D68 VP1-encoding nucleic acid, such as a nucleic acid sequence set forth as SEQ ID NO: 4 (or a portion thereof) or a sequence having at least 80% (for example, at least 85%, at least 90%, at least 95%, at least 96%, at least 97%, at least 98%, at least 99%, or more) sequence identity to SEQ ID NO: 4 or a portion thereof (including, but not limited to GenBank Accession Nos. KP745754 (nucleotides 2341-3267, EV-D68 isolate NY130), KP745753 (nucleotides 2305-3231, EV-D68 isolate NY126), KP745757 (nucleotides 2354-3280, EV-D68 isolate NY210), KP114662 (nucleotides 2169-3095, EV-D68 isolate EV68_Alberta17390_2014), KP322752 (nucleotides 2292-3218, EV-D68 strain US/CA/14-6089), and KP100793 (nucleotides 2355-3281, EV-D68 strain US/CO/14-94), all of which are incorporated by reference herein as present in GenBank on May 15, 2015) and detecting the amplified VP1 nucleic acid. One of ordinary skill in the art can select appropriate amplification methods. In some examples, the VP1 nucleic acid is amplified with at least one primer that is capable of hybridizing (for example under low, high, or very high stringency conditions) to the nucleic acid sequence set forth as SEQ ID NO: 4 or a sequence having at least 80% (for example, at least 85%, at least 90%, at least 95%, at least 96%, at least 97%, at least 98%, at least 99%, or more) sequence identity to SEQ ID NO: 4. In particular examples, the EV-D68 nucleic acid is reverse transcribed prior to amplification (for example, utilizing RT-PCR methods).

In some examples, the primers and probes disclosed herein are capable of hybridizing under high stringency or very high stringency conditions to a nucleic acid molecule including or consisting of SEQ ID NO: 4 or a nucleic acid sequence with at least 80% sequence identity to SEQ ID NO: 4. One of ordinary skill in the art can determine low, high, or very high stringency conditions for hybridization of a primer or probe (such as a primer or probe disclosed herein) to a nucleic acid sequence (such as a sequence with at least 80% identity to SEQ ID NO: 4). In some examples, the conditions are for hybridization of a primer or probe to a nucleic acid attached to a solid support. In other examples, the conditions are for hybridization of a primer or probe to a nucleic acid in solution, such as a PCR reaction mixture. In some non-limiting examples, low stringency conditions include hybridization (such as an annealing step in PCR) at a temperature of about 45-50° C. In other non-limiting examples, high stringency conditions include hybridization (such as an annealing step in PCR) at a temperature of about 50-60° C. In further non-limiting examples, very high stringency conditions include hybridization (such as an annealing step in PCR) at a temperature of greater than 60° C. (such as about 60-68° C.). One of ordinary skill in the art can determine appropriate hybridization or annealing conditions (including the degree of hybridization) based on the particular primers or probes and target nucleic acids to be amplified or detected.

Appropriate samples include any conventional biological sample, including clinical samples obtained from a human or animal subject. Suitable samples include all biological samples useful for detection of *enterovirus* infection in subjects, including, but not limited to, cells, tissues (for example, lung, liver, and kidney), autopsy samples, bodily fluids (for example, blood, serum, urine, cerebrospinal fluid, middle ear fluids, bronchoalveolar lavage (BAL), tracheal aspirates, sputum, nasopharyngeal swabs or aspirates, oropharyngeal swabs or aspirates, or saliva), eye swabs, cervical swabs, vaginal swabs, rectal swabs, stool, and fecal samples. In some specific examples, the sample is a nasopharyngeal and/or oropharyngeal swab, nasal wash, respiratory aspirate, BAL, or serum. Isolated nucleic acids (such as isolated viral RNA or reverse-transcribed viral DNA) are also suitable samples for the methods disclosed herein.

Suitable methods for extracting nucleic acids such as RNA and/or DNA from a sample are known to one of skill in the art; such methods will depend upon, for example, the type of sample being tested. Nucleic acids can be extracted using standard methods. For instance, rapid nucleic acid preparation can be performed using a commercially available kit (such as kits and/or instruments from Qiagen (such as DNEASY®, RNEASY®, or QIAAMP® kits), Roche Applied Science (such as MAGNA® Pure kits and instruments), Thermo Scientific (KingFisher mL), bioMérieux (NUCLISENS® NASBA Diagnostics), or Epicentre (MASTERPURE™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances.

In some examples, the disclosed methods include amplifying an EV-D68 VP1 nucleic acid at least 80% identical (for example at least 85%, at least 90%, at least 95%, at least 96%, at least 97%, at least 98%, at least 99%, or 100% identical) to the nucleic acid sequence set forth as SEQ ID NO: 4 or a portion thereof from a sample and detecting the amplified VP1 nucleic acid. Any method of nucleic acid amplification can be utilized. One of ordinary skill in the art can select an appropriate method of amplification. In particular examples, the methods include contacting the sample with at least one primer between 10 and 40 nucleotides in length, wherein the at least one primer is capable of specifically hybridizing to an EV-D68 VP1 nucleic acid at least 80% identical (for example at least 85%, at least 90%, at least 95%, at least 96%, at least 97%, at least 98%, at least 99%, or 100% identical) to the nucleic acid sequence set forth as SEQ ID NO: 4, amplifying the EV-D68 VP1 nucleic acid or a portion thereof to produce an amplified VP1 nucleic acid, and detecting the amplified VP1 nucleic acid, wherein presence of the amplified VP1 nucleic acid indicates presence of EV-D68 virus in the sample from the subject.

A region of an EV-D68 VP1 nucleic acid that is at least about 200, at least about 225, at least about 250, or at least about 270 base pairs in length is amplified to produce an amplified nucleic acid. In some examples, a region that is about 200-300 base pairs in length (for example, about 250-275 base pairs or about 225-275 base pairs in length) is amplified. In one example, the disclosed methods amplify nucleotides corresponding to positions 2518-2789 of SEQ ID NO: 4.

Any nucleic acid amplification method can be used to detect the presence of EV-D68 nucleic acids in a sample. In one specific, non-limiting example, polymerase chain reaction (PCR) is used to amplify an EV-D68 VP1 nucleic acid or portion thereof. In other specific, non-limiting examples, real-time PCR, reverse transcriptase-polymerase chain reaction (RT-PCR), real-time reverse transcriptase-polymerase chain reaction (rRT-PCR), ligase chain reaction, transcription-mediated amplification (TMA), cell cloning, or cell-based DNA cloning is used to amplify the nucleic acids. In a specific example, an EV-D68 VP1 nucleic acid is amplified by rRT-PCR. Exemplary methods for rRT-PCR are provided in Examples 2 and 3.

Additional techniques for nucleic acid amplification are known to those of ordinary skill in the art. Other examples of nucleic acid amplification techniques include quantitative real-time PCR; nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see Eur. Pat. Publ. EP320308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others. Additional amplification techniques include cell cloning and cell-based DNA cloning (see Strachan and Read, *Human Molecular Genetics*, 2$^{nd}$ edition, Wiley-Liss, 1999).

Typically, at least two primers are utilized in the amplification reaction. In some examples, amplification of the EV-D68 nucleic acid involves contacting a sample including a nucleic acid with one or more primers (such as two or more primers) that are capable of specifically hybridizing to and directing the amplification of an EV-D68 VP1 nucleic acid, such as a primer capable of specifically hybridizing to and directing the amplification of an EV-D68 VP1 nucleic acid sequence set forth as SEQ ID NO: 4 or a portion thereof (or a sequence with at least 80% identity to SEQ ID NO: 4 or a portion thereof), for example a primer that is least 90% identical (such as at least 91%, 92%, 93%, 94%, 95%, 96%, 97%, 98%, 99%, or 100% identical) to the nucleotide sequence set forth as SEQ ID NO: 1 or SEQ ID NO: 2, or the reverse complement thereof. In one example, an EV-D68 VP1 nucleic acid is amplified utilizing a pair of primers, such as a forward primer at least 90% identical to SEQ ID NO: 1 and a reverse primer at least 90% identical to SEQ ID NO: 2, such as a forward primer comprising, consisting essentially of, or consisting of SEQ ID NO: 1 and a reverse primer comprising, consisting essentially of, or consisting of SEQ ID NO: 2.

Detecting the amplified product can be by any method known to one of ordinary skill in the art. In some examples, the amplified VP1 nucleic acid is detected by gel electrophoresis (such as slab gel electrophoresis or capillary gel electrophoresis) or by sequencing. In some examples, one or more of the disclosed primers include a detectable label. In other examples, the amplified VP1 nucleic acid is detected by the use of one or more detectably labeled probes that are complementary to and specifically hybridize to the amplified nucleic acid sequence or a portion thereof. Thus, the presence, amount, and/or identity of the amplified product can be detected by hybridizing a detectably labeled probe, such as a fluorescently labeled probe, complementary to the amplified product or a portion thereof. In one example, an EV-D68 VP1 probe includes an oligonucleotide (such as a detectably labeled oligonucleotide) at least 90% identical to SEQ ID NO: 3, such as a probe comprising, consisting essentially of, or consisting of the nucleotide sequence of SEQ ID NO: 3, or the reverse complement thereof.

In one embodiment, the detection of a target nucleic acid sequence of interest, such as an EV-D68 VP1 nucleic acid, includes the combined use of PCR amplification and a labeled probe such that the product is measured using real-time PCR (such as real-time RT-PCR). Thus, in some examples, the disclosed methods include contacting a sample with a forward primer capable of specifically amplifying an EV-D68 VP1 nucleic acid (such as SEQ ID NO: 1), a reverse primer capable of specifically amplifying an EV-D68 VP1 nucleic acid (such as SEQ ID NO: 2), and a detectably labeled probe capable of specifically hybridizing to an EV-D68 VP1 nucleic acid (such as SEQ ID NO: 3) under conditions sufficient for amplification of the nucleic acid by the primers and hybridization of the probe to the nucleic acid and detecting a change in signal from the probe, thereby detecting presence of EV-D68 in the sample. In some examples, conditions sufficient for amplification of the EV-D68 VP1 nucleic acid include contacting the sample with the detectably labeled probe and primers in a solution or reaction mixture including enzymes (e.g., reverse-transcriptase and DNA polymerase), buffer(s), metal ion(s), and/or salt(s). Exemplary reaction mixtures include SuperScript® III reaction mix and enzymes (ThermoFisher Scientific, Waltham, Mass.), gScript™ XLT One-Step RT-qPCR ToughMix® reaction mix (Quanta Biosciences, Beverly, Mass.), and Ag-Path-ID™ One-Step RT-PCR kit (ThermoFisher Scientific, Waltham, Mass.). One of skill in the art can identify additional reagents and conditions suitable for the methods disclosed herein.

In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In still further embodiments, the detection of amplified target nucleic acid sequence of interest includes the hybridization of a labeled amplified target nucleic acid to one or more probes that are arrayed in a predetermined array with an addressable location and that are complementary to the amplified target nucleic acid.

In some embodiments, the primer or probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with an amplified EV-D68 reaction mixture or product (either subsequently or concurrently with amplification), and hybridization is determined. In some examples, the hybridization results in a detectable change in signal such as in increase or decrease in signal, for example from a labeled probe. Thus, in some examples, detecting hybridization comprises detecting a change in signal from a labeled probe during or after hybridization relative to signal from the label before hybridization.

The methods disclosed herein specifically detect EV-D68 in a sample (for example, specifically detect an EV-D68 VP1 nucleic acid in a sample). In some embodiments, the disclosed methods detect EV-D68 in a sample, but do not detect other enteroviruses, such as EV-A, EV-B, or EV-C viruses or RV-A or RV-B viruses. In additional embodiments, the disclosed methods detect EV-D68 in a sample, but do not detect other EV-D viruses, such as EV-D70, EV-D94, EV-D111, or EV-D120. In further embodiments, the disclosed methods specifically detect EV-D68 of the 2014 EV-D68 North America lineage (including, but not limited to GenBank Accession Nos. KM851225 (EV-D68 strain US/MO/14-18947), KP745754 (EV-D68 isolate NY130), KP745753 (EV-D68 isolate NY126), KP745757 (EV-D68 isolate NY210), KP114662 (EV-D68 isolate EV68_Alberta17390_2014), KP322752 (EV-D68 strain US/CA/14-6089), and KP100793 (EV-D68 strain US/CO/14-94), all of which are incorporated by reference herein as present in GenBank on May 15, 2015). Thus, in some examples, the disclosed methods detect presence of 2014 EV-D68 North America lineage virus in a sample, but do not detect EV-D68 from other circulating EV-D68 lineages, for example lineages similar to those circulating in the U.S. in about 2009-2010 (exemplified by GenBank Accession No. KM851231 (US/KY/14-18953), incorporated by reference herein as present in GenBank on May 15, 2015). In some examples, these other EV-D68 lineages have a codon deletion compared to 2014 EV-D68 North America lineage viruses in the reverse primer site (FIG. 3). Additional exemplary EV-D68 viruses with this deletion include GenBank Accession Nos. KP153538 (ITA/23341/14), JQ924864 (China 2011), and JX898786 (China 2012), all of which are incorporated herein by reference as present in GenBank on May 15, 2015. In an another example, the disclosed methods detect presence of 2014 EV-D68 North America lineage virus in a sample, but do not detect EV-D68 Fermon strain.

IV. Primers and Probes

Primers (such as isolated nucleic acid primers) and probes (such as isolated nucleic acid probes) suitable for use in the disclosed methods are described herein. In some examples, the primers and probes are suitable for detection of EV-D68 nucleic acids using real-time PCR assays described herein.

In some embodiments, the disclosed primers and/or probes are between 10 and 60 nucleotides in length, such as 10, 11, 12, 13, 14, 15, 16, 17, 18, 19, 20, 21, 22, 23, 24, 25, 26, 27, 28 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length and are capable of specifically hybridizing to, and in some examples, specifically amplifying an EV-D68 VP1 nucleic acid. In some examples, the primers and/or probes are at least 10, 15, 20, 25, 30, 35, 40, 45, 50, 55, or 60 nucleotides in length. In other examples, the primers and/or probes may be no more than 10, 15, 20, 25, 30, 35, 40, 45, 50, 55, or 60 nucleotides in length.

In some examples, the disclosed primers include primers for amplification of EV-D68 nucleic acids (such as EV-D68 VP1 nucleic acids), including primers comprising a nucleic acid sequence with at least 90% sequence identity (for example, at least 91%, 92%, 93%, 94%, 95%, 96%, 97%, 98%, 99%, or 100% identity) to CAAACTCGCACAGTGATAAAYCARCA (SEQ ID NO: 1) or GTATTATTACTACTACCATTCACNGCNAC (SEQ ID NO: 2). In some examples, the disclosed primers comprise, consist essentially of, or consist of the nucleic acid sequence of SEQ ID NO: 1 or SEQ ID NO: 2.

Also disclosed herein are probes that specifically hybridize to EV-D68 nucleic acids (such as EV-D68 VP1 nucleic acids), including probes comprising a nucleic acid sequence with at least 90% sequence identity (for example, at least 91%, 92%, 93%, 94%, 95%, 96%, 97%, 98%, 99%, or 100% identity) to GTCCATTTGAAAAAGTTCTTGTC (SEQ ID NO: 3). In some examples, the disclosed probes comprise, consist essentially of, or consist of the nucleic acid sequence of SEQ ID NO: 3.

In some examples, the probe includes a detectable label, such as a fluorophore. In particular examples, the probe (e.g., SEQ ID NO: 3) includes a fluorophore at the 5' or 3' end, which is FAM in one non-limiting example. In other examples, the probe (e.g., SEQ ID NO: 3) includes a fluorescence quencher at the 5' or 3' end, such as a dark quencher, which is BHQ1 in one non-limiting example. In one non-limiting example, the probe comprises or consists of 5'-FAM-GTCCATTTGAAAAAGTTCTTGTC-BHQ1-3' (SEQ ID NO: 3). In other examples, the probe (e.g., SEQ ID NO: 3) includes a fluorophore at the 5' or 3' end, which is CY5 in one non-limiting example. In other examples, the probe (e.g., SEQ ID NO: 3) includes a fluorescence quencher at the 5' or 3' end, such as a dark quencher, which is BHQ2 in one non-limiting example. In one non-limiting example, the probe comprises or consists of 5'-CY5-GTC-CATTTGAAAAAGTTCTTGTC-BHQ2-3' (SEQ ID NO: 3). Additional fluorophore/quencher combinations that could be utilized with the probes disclosed herein (such as SEQ ID NO: 3) include FAM-TAMRA, TET-BHQ1, TET-TAMRA, JOE-BHQ1, JOE-TAMRA, HEX-BHQ2, CY3-BHQ2, ROX-BHQ2, Texas Red-BHQ2, Quasar670-BHQ2, and CY5-BHQ3. One of ordinary skill in the art can identify other fluorophore/quencher pairs that could also be utilized with the disclosed probes.

Although exemplary primer and probe sequences are provided herein, the primer and/or probe sequences can be varied slightly by moving the primer a few nucleotides upstream or downstream from the nucleotide positions that they hybridize to on the target nucleic molecule acid, provided that the probe and/or primer is still specific for the target nucleic acid sequence. For example, variations of the primers and probe disclosed as SEQ ID NOs: 1-3 can be made by "sliding" the probe or primer a few nucleotides 5' or 3' from their positions, and such variations will still be specific for the respective target nucleic acid sequence.

Also provided by the present disclosure are primers and/or probes that include variations to the nucleotide sequences shown in any of SEQ ID NOs: 1-3, as long as such variations permit amplification and/or detection of the target nucleic acid molecule. For example, a primer or probe can have at least 90% sequence identity such as at least 91%, 92%, 93%, 94%, 95%, 96%, 97%, 98%, or 99% identity to a nucleic acid including the sequence shown in any of SEQ ID NOs: 1-3. In such examples, the number of nucleotides does not change, but the nucleic acid sequence shown in any of SEQ ID NOs: 1-3 can vary at a few nucleotides, such as changes at 1, 2, 3, 4, 5, or 6 nucleotides.

The present application also provides primers and/or probes that are slightly longer or shorter than the nucleotide sequences shown in any of SEQ ID NOs: 1-3, as long as such deletions or additions permit specific amplification and/or detection of the desired target nucleic acid molecule. For example, a primer or probe can include a few nucleotide deletions or additions at the 5'- or 3'-end of the probe or primers shown in any of SEQ ID NOs: 1-3, such as addition or deletion of 1, 2, 3, 4, 5, or 6 nucleotides from the 5'- or 3'-end, or combinations thereof (such as a deletion from one end and an addition to the other end). In such examples, the number of nucleotides changes.

Also provided are primers and/or probes that are degenerate at one or more positions (such as 1, 2, 3, 4, 5, or more positions), for example, a primer or probe that includes a mixture of nucleotides (such as 2, 3, or 4 nucleotides) at a specified position in the oligonucleotide. In other examples, the primers or probes disclosed herein include one or more synthetic bases or alternative bases (such as inosine). In other examples, the primers or probes disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the primers or probes disclosed herein include a minor groove binder conjugated to the 5' or 3' end of the oligonucleotide (see, e.g., U.S. Pat. No. 6,486,308).

V. Kits

The nucleic acid primers and/or probes disclosed herein can be supplied in the form of a kit for use in the detection or amplification of EV-D68 nucleic acids (such as an EV-D68 VP1 nucleic acid). In such a kit, an appropriate amount of one or more of the disclosed nucleic acid primers and/or probes (such as one or more of SEQ ID NOs: 1-3) are provided in one or more containers or in one or more individual wells of a multiwell plate or card. A nucleic acid primer or probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid primers (for example, 1, 2 or more primers) and/or labeled or unlabeled nucleic acid probes (for example, 1, 2, or more probes) for use in amplification and/or detection of EV-D68 nucleic acids.

One or more positive, negative, and/or internal control primers and/or nucleic acids also may be supplied in the kit. Exemplary RNA extraction and internal RT-PCR controls include primers, probes, and/or nucleic acids for amplification of human target nucleic acids such as human β-actin or RNase P (see, e.g., Emery et al., *Emerg. Infect. Dis.* 10:311-316, 2004). Exemplary positive controls include primers, probes, and/or nucleic acids for amplification of known EV-D68 viral nucleic acids. Additional positive control samples that may be supplied in the kit include EV-D68 genomic RNA, in vitro transcribed EV-D68 RNA (such as EV-D68 VP1 RNA), or reverse-transcribed EV-D68 VP1 cDNA. One of skill in the art can select suitable controls for the assays disclosed herein.

In some examples, one or more primers and/or probes (such as a forward primer, reverse primer, and probe), are provided in pre-measured single use amounts in individual, typically disposable, tubes, wells, or equivalent containers. In this example, the sample to be tested for the presence of the target nucleic acids can be added to the individual tube(s) or well(s) and amplification and/or detection can be carried out directly.

The disclosed kits may also include additional reagents for the detection and/or amplification of EV-D68 nucleic acids, such as buffer(s), nucleotides (such as dNTPs), enzymes (such as DNA polymerase and/or reverse transcriptase), or other suitable reagents. The additional reagents may be in separate container(s) from the one or more primer(s) and/or probe(s) or may be included in the same container as the primer(s) and/or probe(s).

In particular examples, the kit includes a set of primers including SEQ ID NOs: 1 and 2, and a probe including SEQ ID NO: 3. In particular examples, the probe included in the kit comprises or consists of SEQ ID NO: 3 with a 5' fluorophore (such as FAM or CY5) and a 3' quencher (such as BHQ1 or BHQ2). In some examples, the probe included in the kit comprises or consists of 5'-FAM-GTCCATTT-GAAAAAGTTCTTGTC-BHQ1-3' (SEQ ID NO: 3) or 5'-CY5-GTCCATTTGAAAAAGTTCTTGTC-BHQ2-3' (SEQ ID NO: 3).

The present disclosure is illustrated by the following non-limiting Examples.

Example 1

Primer and Probe Design

Figure 2:
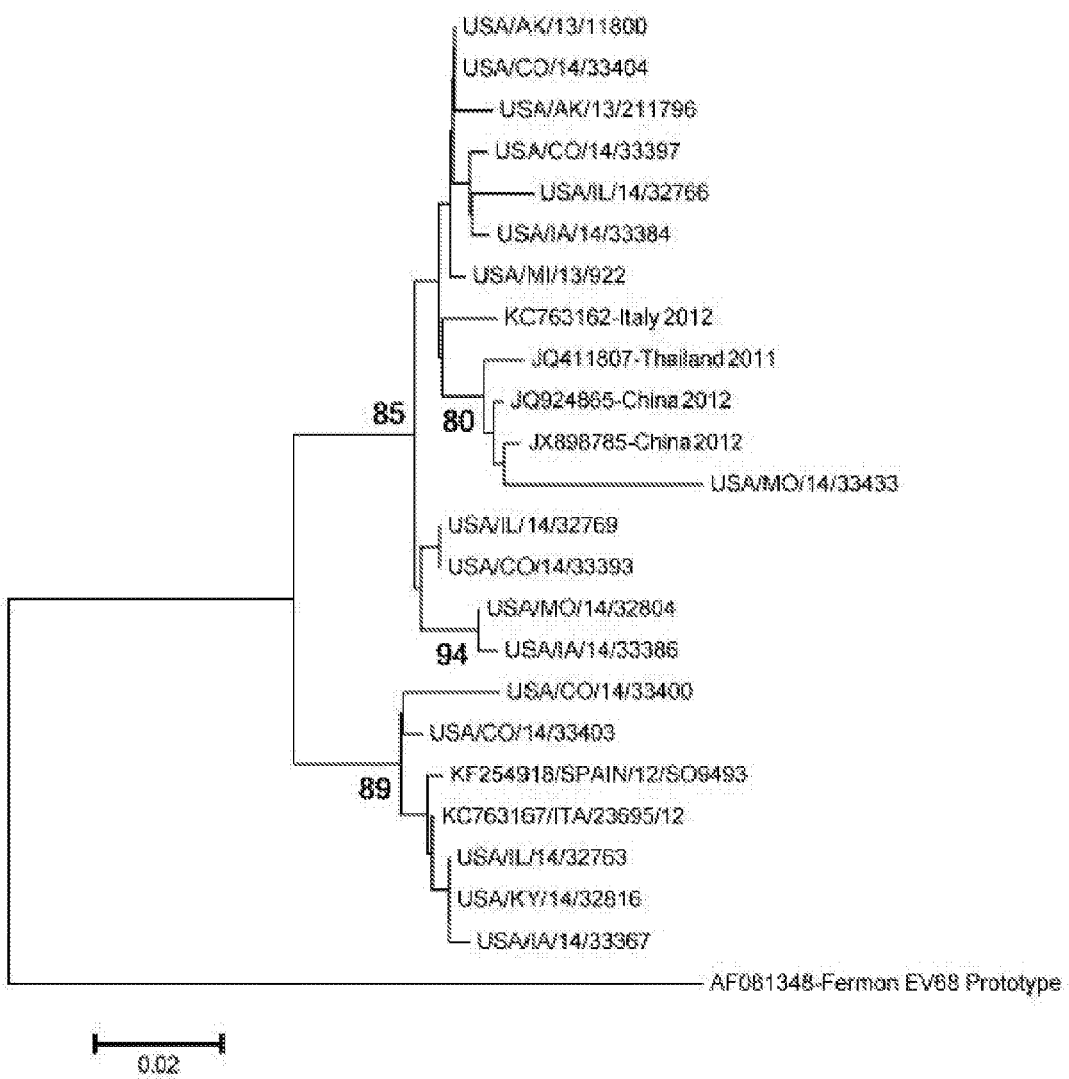
FIG. 2 is a phylogenetic tree showing evolutionary relationships of US2014 EV-D68s to recent viruses from GenBank and 2013 EV-D68s from the CDC diagnostic database. The evolutionary history was inferred using the Neighbor-Joining method. The optimal tree with the sum of branch length=0.33164807 is shown. The percentage of replicate trees in which the associated taxa clustered together in the bootstrap test (500 replicates) are shown next to the branches (values≥80 shown). The tree is drawn to scale, with branch lengths in the same units as those of the evolutionary distances used to infer the phylogenetic tree. The evolutionary distances were computed using the Kimura 2-parameter method and are in the units of the number of base substitutions per site. The analysis involved 24 nucleotide sequences. Codon positions included were 1st+2nd+3rd+Noncoding. All ambiguous positions were removed for each sequence pair. There were a total of 336 positions in the final dataset. Evolutionary analyses were conducted in MEGA5 software.

The EV-D68-specific assay primers and probe were designed from an alignment of 576 EV-D68 partial VP1 sequences from the 2014 US outbreak (including GenBank Accession Nos. KM851225 through KM851231; Brown et al., *Genome Announc.* 2:e01201-14, 2014) and from GenBank. The other related EV-D68 strains with at least partial VP1 sequences included those from the United States in 2013, Spain in 2012 (GenBank Accession No. KF254918), Italy in 2012 (GenBank Accession Nos. KC763167, KC763162), China in 2012 (GenBank Accession Nos. JX898785, JQ924865), and Thailand in 2011 (GenBank Accession No. JQ411807). Sequences were aligned using MEGA 5.0 software, with default parameters for the CLUSTAL W alignment. Co-circulation of at least three separate EV-D68 clusters were detected. EV-D68 within the major cluster (FIG. 2, node with bootstrap value of 85) accounted for 92.4% of patients and EV-D68 within the minor cluster (FIG. 2, node with bootstrap value of 89) accounted for 7.3% of patients. These two clusters are collectively referred to herein as 2014 EV-D68 North American lineage(s) and are detected by the assay described herein.

"Nearest neighbors," members of EV-D other than EV-D68, included EV-D70, EV-D94, EV-D111, and EV-D120. EV-D111 was first detected in chimpanzees in Cameroon, but it was later identified in human stool specimens (unpublished data). EV-D120, isolated from gorillas and a chimpanzee, in Cameroon and the Democratic Republic of Congo, respectively, was not available for testing. To date this virus has not been detected in humans.

Primer and probe sites were first visualized in an amino acid alignment of all contemporary EV-D species identified to date (EV-D68, GenBank Accession No. ABL61317; EV-D70, GenBank Accession No. BAA18891; EV-D94, GenBank Accession Nos. ABK88241 and ABL61316; EV-D111, GenBank Accession No. ADY76793, and EV-D120, GenBank Accession Nos. AGU46444 and AGU46445) and 2014 U.S. EV-D68 stains, plus the older prototype strain Fermon (GenBank Accession No. AAR98503). VP1 motifs that differentiated EV-D68 from other EV-D viruses were chosen. All available EV-D68 VP1 amino acid sequences were aligned to analyze conservation of the motifs and primer and probe design was finalized.

The amino acid motif for the forward primer (AN887, Table 1) is largely conserved in EV-D, except for the carboxyl glutamine residue that is shared by EV-D68 and EV-D94 only. Conservation of the probe motif is high for all EV-D. US 2014 EV-D68 strains and other contemporary EV-D68 strains in GenBank all have a unique aspartic acid residue and a carboxyl lysine residue shared with EV-D94 only. The amino acid motif for the reverse primer (AN893, Table 1) is specific for contemporary EV-D68 viruses (see, e.g., FIG. 3) and is somewhat different in the Fermon strain, but significantly different from all other EV-D.

Degeneracy in the sense and antisense primers was kept to a minimum in the design. Extension end (3' end) degeneracy for AN887 is four-fold, while for AN893 degeneracy is sixteen-fold. The probe (AN890, Table 1) is non-degenerate. From the large nucleotide alignment of recent EV-D68s from the US, Asia, and Europe, codon usage was inferred for EV-D68-specific primer and probe design. As designed, the EV-D68 assay is predicted to detect 2014 North American lineage EV-D68 viruses in the alignment based on the in silico analysis.

TABLE 1

Primer and Probe Sequences

| ID | Location[a] | Nucleotide Sequence (5'-3') | SEQ ID NO: | Amino Acid Motif | SEQ ID NO: |
|---|---|---|---|---|---|
| AN887 (forward) | 2518-2543 | CAAACTCGCACAGTGAT AAAYCARCA | 1 | QTRTVINQH | 5 |
| AN893 (reverse) | 2789-2761 | GTATTATTACTACTACC ATTCACNGCNAC | 2 | VAVNGSSNNT | 6 |
| AN890 (probe) | 2669-2647 | GTCCATTTGAAAAAGTT CTTGTC | 3 | DKNFFKWT | 7 |

[a]Position relative to the 2014 outbreak strain US/MO/14-18947 (GenBank Accession No. KM851225)

The amplicon size of 272 nucleotides is larger than ideal for a real-time RT-PCR assay. In addition, probe has a G at the 5' end. Both compromises were made due to the limited VP1 sequence span available, in the interest of assuring a highly specific assay with little or no cross-reactivity with other EV-Ds.

Example 2

Diagnostic Sensitivity and Specificity of Real-Time PCR Assay

Real-time PCR was performed using the primers and probe described in Example 1. Reactions (25 µl volume) included 1× SUPERSCRIPT III reaction mix, 1.25 mM $MgSO_4$, 0.4 μM AN887, 0.4 μM AN893, 0.2 μM AN890 (with 5' FAM and 3' BHQ1), 1× SuperScript® III reverse transcriptase/Platinum Taq mix, and 5 μl specimen RNA. Optimum thermocycling parameters were determined empirically. The final conditions were reverse transcription at 50° C. for 30 minutes, followed by 1 minute at 95° C., and 45 cycles of 15 seconds at 95° C., 1 minute at 55° C., and 5 seconds at 72° C. on an ABI 7500 platform. Equivalent results were achieved with AB7500, AB7500 Fast, and AB7500 Fast Dx platforms (Applied Biosystems).

EV-D cell culture isolates were tested with the EV-D68-specific assay. Undiluted RNA extracted from cell culture supernatants was tested. As shown in Table 2, all EV isolates except for EV-D68 were negative in the EV-D68-specific assay. EV-D120, isolated from gorillas and a chimpanzee, in Cameroon and the Democratic Republic of Congo, respectively, was not available for testing. To date, this virus has not been detected in humans.

Other common respiratory pathogens circulating during EV season were also tested. These included adenovirus C1 (Ad71), coronaviruses 229E, OC43, and MERS, human metapneumovirus (CAN99-81), Influenza A (H1N1 and H3Na), influenza B, parainfluenza viruses 1 (C35), 2 (Greer), 3 (C-43), and 4a (CH 19503), respiratory syncytial virus (Long A), Dengue virus types 1-4, Eastern equine encephalitis virus, Western equine encephalitis virus, Colorado tick fever virus, Powassan virus, Japanese encephalitis virus, West Nile virus, yellow fever virus, Lacrosse encephalitis virus, St. Louis encephalitis virus, Chikgungunya virus, herpes simplex viruses 1 and 2, varicella zoster virus, measles virus, mumps virus, *Neisseria meningitides, Listeria monocytogenes, Escherichia coli, Bacillus cereus, Lactobacillus acidophilus*, and *Cryptococcus neoformans*. One hundred rhinovirus (RV) species A and B (RV-A1, A2, A7-A13, A15, A16, A18-25, A28-34, A36, A38-41, A43, A45-47, A49-51, A53-68, A71, A73-78, A80, A82, A85, A88-90, A04, A96, and A100; RV-B3-B6, B14, B17, B26, B27, B35, B37, B42, B48, B52, B69, B70, B72, B79, B83, B84, B86, B91-93, B97, and B99) were also tested with the EV-D68-specific assay using undiluted RNA from cell culture supernatants. All assay results were negative.

TABLE 2

| Analytical specificity of EV-D68-specific assay | |
|---|---|
| EV-D Cell Culture Isolate | EV-D68-Specific Assay Result |
| EV-D70, Prototype J670/1971 | Negative |
| EV-D94, Nigeria 2010, a | Negative |
| EV-D94, Nigeria 2010, b | Negative |
| EV-D94, Angola 2012 | Negative |
| EV-D111, Angola 2012, a | Negative |
| EV-D111, Angola 2012, b | Negative |
| EV-D68, Prototype Fermon 1962 | Negative |
| EV-D68, USA/MO/14-18947 | Positive |

A set of 242 respiratory specimens tested with the "gold standard" EV VP1 sequencing assay (Nix et al., *J. Clin. Microbiol.* 44:2698-2704, 2006) during the outbreak investigation. Of these, 69 were identified as EV-D68 and 68 were EV-D68-negative by sequencing. These were used to evaluate the EV-D68-specific assay. There was excellent concordance between the two assays: the EV-D68-specific assay identified all 69 EV-D68s that were identified by VP1 sequencing (100% sensitivity) and amplified only three of 68 samples that were negative in the VP1 sequencing assay (96% specificity) (Table 3). Two of the samples that were positive in the EV-D68 real-time PCR, but negative by sequencing, both had high Ct values in the EV-D68-specific assay (40.1 and 40.9). Absolute sensitivity (limit of detection) for the EV VP1 protocol was less than 10 genome copies (Nix et al., *J. Clin. Microbiol.* 44:2698-2704, 2006).

TABLE 3

Sensitivity and specificity of EV-D68-specific assay versus VP1 PCR/sequencing assay

| | | EV VP1 Standard Typing Assay | | |
|---|---|---|---|---|
| | | + | − | |
| EV-D68-Specific Assay | + | (True Positive) 75 | (False Positive) 3 | Positive Predictive Value 96.2% (89.3%-98.7%) |
| | − | (False Negative) 0 | (True Negative) 164 | Negative Predictive Value 100% (97.7%-100%) |
| | | Sensitivity 100% (95.1%-100%) | Specificity 98.2% (94.9%-99.4%) | |

Assuming that the analytical sensitivity of the two assays is approximately equal, the two specimens that were positive by the real-time PCR assay, but negative by sequencing were likely to be low-titer EV-D68 samples (true positives), with concentrations near the limit of detection of both assays. The other sample that was positive in the EV-D68 real-time PCR but negative by sequencing appeared to represent a co-infection, with a clear mixture of virus sequences visible in the sequence analysis chromatograms and a relatively low Ct value of 31.2 in the EV-D68-specific assay. The virus identified by GenBank nucleotide BLAST of the readable portion of the sequence was RV-A10.

The EV-D68 rRT-PCR limit of detection was determined with a titered EV-D68 isolate RNA dilution series and compared to limits of detection of the "gold-standard" EV VP1 RT-snPCR assay (Nix et al., *J. Clin. Microbiol.* 44:2698-2704, 2006). Results are shown in Table 4.

TABLE 4

Limits of detection

| RNA Dilution | Concentration ($CCID_{50}/5$ µl)* | Result EV-D68 rRT-PCR | Result VP1 RT-snPCR |
|---|---|---|---|
| $10^{-1}$ | $10^{4.9}$ | 3/3 Positive | 3/3 Positive |
| $10^{-2}$ | $10^{3.9}$ | 3/3 Positive | 3/3 Positive |
| $10^{-3}$ | $10^{2.9}$ | 3/3 Positive | 3/3 Positive |
| $10^{-4}$ | $10^{1.9}$ | 3/3 Positive | 3/3 Positive |
| $10^{-5}$ | $10^{0.9}$ | 3/3 Positive | 3/3 Positive |
| $10^{-6}$ | $10^{-0.1}$ | 3/3 Positive | 3/3 Positive |
| $10^{-7}$ | $10^{-1.1}$ | 3/3 Positive | 3/3 Positive |
| $10^{-8}$ | $10^{-2.1}$ | 1/3 Positive | 2/3 Positive |
| $10^{-9}$ | $10^{-3.1}$ | 0/3 - Negative | 0/3 - Negative |

*$CCID_{50}$, cell culture infectious dose 50% end point

One advantage of specific assays is the ability to clearly detect the specific target in a mixture with another *enterovirus* or rhinovirus. Undiluted RNA extracted from cell culture supernatants from EV-D68-Fermon, other viruses in EV-D, and 101 rhinovirus prototype strains were also tested. For all of these isolates the EV-D68-specific assay was negative, confirming specificity for currently circulating EV-D68 strains, including the 2014 EV-D68 North America lineage.

Example 3

Real-Time RT-PCR Assay for EV-D68 with Modified Probe Labeling

This example describes a real-time RT-PCR assay for EV-D68 utilizing a probe with modified labeling compared to that utilized in Example 2.

Two 2014 EV-D68 viral RNAs, extracted from titered virus stocks, were serially diluted and assayed. The two EV-D68 viruses represent the major and minor strains (major-USA/MO/14-18949 and minor-USA/MO/14-18952) that circulated during the 2014 US EV-D68 outbreak. Real-time PCR was performed using the primers and probe described in Example 1. Reactions (20 µl volume) included 10 µl 2× Reaction Buffer (gScript™ XLT One-Step RT-qPCR Tough-Mix®; Quanta Biosciences, Beverly, Mass.), 0.5 µM AN887, 0.5 µM AN893, 0.15 µM AN890 (with 5' CY5 [or equivalents like Q670 or Beckman D4] and 3' BHQ2), 2.4 µl PCR grade water, and 5 µl specimen RNA. Optimum thermocycling parameters were determined empirically. The final conditions were reverse transcription at 50° C. for 30 minutes, followed by 1 minute at 95° C., and 45 cycles of 15 seconds at 95° C., and 50 seconds at 55° C. on an ABI 7500 Fast platform. Equivalent results were achieved with the AB7500 Fast Dx platforms (Applied Biosystems). Data from an analytical sensitivity (limit of detection) range finding experiment are shown in Table 5.

TABLE 5

Limits of Detection

| Virus Identification | RNA Dilution ($CCID_{50}$ per 5 µl)* | AB 7500 FAST Results from 3 replicates (Average Ct) | AB 7500 FAST DX Results from 3 replicates (Average Ct) |
|---|---|---|---|
| USA/MO/14-18949 | $1 \times 10^{-5}$ (0.80000) | 3/3 (27.7) | 3/3 (25) |
| | $1 \times 10^{-6}$ (0.08000) | 3/3 (30) | 3/3 (28) |
| | $1 \times 10^{-7}$ (0.00800) | 3/3 (33) | 3/3 (31) |
| | $1 \times 10^{-8}$ (0.00080) | 3/3 (35.3) | 3/3 (34.3) |
| | $1 \times 10^{-9}$ (0.00008) | 1/3 (39) | 2/3 (36) |
| USA/MO/14-18952 | $1 \times 10^{-5}$ (0.90000) | 3/3 (26) | 3/3 (24) |
| | $1 \times 10^{-6}$ (0.09000) | 3/3 (29.3) | 3/3 (28.3) |
| | $1 \times 10^{-7}$ (0.00900) | 3/3 (32.7) | 3/3 (31.3) |
| | $1 \times 10^{-8}$ (0.00090) | 3/3 (36.3) | 3/3 (34) |
| | $1 \times 10^{-9}$ (0.00009) | 1/3 (40) | 3/3 (38) |

*$CCID_{50}$, cell culture infectious dose 50%

Example 4

Real-Time RT-PCR Assay for Detecting EV-D68 in a Sample

This example describes exemplary methods for detecting EV-D68 in a sample utilizing a real-time PCR assay. However, one skilled in the art will appreciate that methods that deviate from these specific methods can also be used to successfully detect EV-D68 nucleic acids in a sample.

One or more samples from a subject (such as a subject suspected of being infected with EV-D68) are provided, such as nasal washes, NP swabs, OP swabs, or dual NP/OP swabs. RNA is extracted from the sample, for example utilizing a commercially available RNA extraction kits or instruments. Exemplary suitable commercially available kits or instruments include QIAAmp® Viral RNA Mini Kit (Qiagen, Valencia, Calif.) or NucliSENS® easyMAG® instrument (bioMerieux, Durham, N.C.); however, one of ordinary skill in the art can select other suitable kits or instruments for RNA extraction.

Real-time RT-PCR is performed in a 20 µl reaction volume including 1× (final) gScript™ XLT One-Step RT-qPCR ToughMix® (Quanta Biosciences, Beverly, Mass.), 0.5 µM forward primer (CAAACTCGCACAGTGA-TAAAYCARCA; SEQ ID NO: 1), 0.5 µM reverse primer (GTATTATTACTACTACCATTCACNGCNAC; SEQ ID NO: 2), 0.15 µM probe (CY5-GTCCATTTGAAAAAGT-TCTTGTC-BHQ2; SEQ ID NO: 3), and 5 µl specimen RNA. Thermocycling is carried out with reverse transcription at 50° C. for 30 minutes, followed by 1 minute at 95° C., and 45 cycles of 15 seconds at 95° C. and 50 seconds at 55° C. The thermocycling is carried out on an AB7500 Fast or AB7500 Fast Dx platform in some examples; however, other real-time PCR platforms can also be used. In addition, alternate real-time PCR reaction mixtures may be utilized in the assay, including, but not limited to SuperScript® III reaction mix and enzymes or Ag-Path-ID™ One-Step RT-PCR kit (ThermoFisher Scientific, Waltham, Mass.).

An EV-D68 positive sample is one with a Ct<43. Samples with Ct≥43 and <45 are considered equivocal and may be retested. In some circumstances, positive samples may also be independently confirmed with a second methodology, such as the EV VP1 RT-snPCR assay (Nix et al., *J. Clin. Microbiol.* 44:2698-2704, 2006).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting presence of human *enterovirus* D68 (EV-D68) in a sample, comprising:
   contacting the sample with:
   a forward primer and a reverse primer capable of amplifying an EV-D68 viral protein 1 (VP1) nucleic acid or portion thereof, wherein the forward primer consists of the nucleic acid sequence of SEQ ID NO: 1 and the reverse primer consists of the nucleic acid sequence of SEQ ID NO: 2; and
   a detectably labeled probe consisting of the nucleic acid sequence of SEQ ID NO: 3 and a detectable label,
   under conditions sufficient for amplification of the EV-D68 VP1 nucleic acid by the forward and reverse primer and hybridization of the probe to the EV-D68 VP1 nucleic acid; and
   detecting the amplification of the EV-D68 VP1 nucleic acid and/or hybridization of the probe to the EV-D68 VP1 nucleic acid, thereby detecting presence of human *enterovirus* D68 in the sample.

2. The method of claim 1, wherein the detectably labeled probe comprises at least one fluorophore.

3. The method of claim 2, wherein the detectably labeled probe comprises a donor fluorophore, an acceptor fluorophore, or a combination thereof.

4. The method of claim 3, wherein the detectably labeled probe comprises the donor fluorophore FAM or CY5 and the acceptor fluorophore BHQ1 or BHQ2.

5. The method of claim 4, wherein the detectably labeled probe consists of FAM-GTCCATTTGAAAAAGTTCTTGTC-BHQ1 (SEQ ID NO: 3) or CY5-GTCCATTTGAAAAAGTTCTTGTC-BHQ2 (SEQ ID NO: 3).

6. The method of claim 1, wherein the sample comprises isolated DNA, isolated RNA, serum, a nasal wash, a respiratory aspirate, a nasopharyngeal swab, or an oropharyngeal swab.

7. An isolated probe consisting of the nucleic acid sequence of SEQ ID NO: 3 and a detectable label.

8. The isolated probe of claim 7, wherein the detectable label comprises one or more fluorophores, chromogenic moieties, haptens, affinity tags, or radioactive isotopes.

9. The isolated probe of claim 8, wherein the detectable label comprises a donor fluorophore, an acceptor fluorophore, or a combination thereof.

10. The isolated probe of claim 9, wherein the detectable label comprises the donor fluorophore FAM or CY5 and the acceptor fluorophore BHQ1 or BHQ2.

11. The isolated probe of claim 10, wherein the probe consists of FAM-GTCCATTTGAAAAAGTTCTTGTC-BHQ1 (SEQ ID NO: 3) or CY5-GTCCATTTGAAAAAGT-TCTTGTC-BHQ2 (SEQ ID NO: 3).

12. A kit for detecting human *enterovirus* D68 in a sample, comprising:
    a detectably labeled probe consisting of the nucleic acid sequence of SEQ ID NO: 3 and a detectable label;
    a forward primer consisting of the nucleic acid sequence of CAAACTCGCACAGTGATAAAYCARCA (SEQ ID NO: 1); and
    a reverse primer consisting of the nucleic acid sequence of GTATTATTACTACTACCATTCACNGCNAC (SEQ ID NO: 2).

13. The kit of claim 12, wherein the detectably labeled probe consists of FAM-GTCCATTTGAAAAAGTTCTT-GTC-BHQ1 (SEQ ID NO: 3) or CY5-GTCCATTT-GAAAAAGTTCTTGTC-BHQ2 (SEQ ID NO: 3).

14. The kit of claim 13, further comprising:
    a detectably labeled probe capable of hybridizing to a human RNase P nucleic acid;
    a forward primer capable of hybridizing to the human RNase P nucleic acid; and
    a reverse primer capable of hybridizing to the human RNase P nucleic acid.

* * * * *

```
                           SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 1
caaactcgca cagtgataaa ycarca                                            26

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 2
gtattattac tactaccatt cacngcnac                                         29

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 3
gtccatttga aaagttctt gtc                                                23

<210> SEQ ID NO 4
<211> LENGTH: 927
<212> TYPE: DNA
<213> ORGANISM: Enterovirus 68

<400> SEQUENCE: 4
ctagaccatt tacatgcagc agaggcagcc taccagatcg agagcatcat caaaacagcg        60
accgacactg tgaaaagtga gattaatgct gaacttggtg tggtccctag cttaaatgca       120
gttgaaacag gtgcaacttc taacactgaa ccagaagaag ccatacaaac tcgcacagtg       180
ataaatcagc acggtgtatc cgagactcta gtggagaatt ttctcagtag agcagctttg       240
gtatcaaaga gaagtttttga atacaaagat catacttcgt ctacagcacg agcagacaag       300 aacttttttca aatggacaat taacaccaga tcctttgtac agttaagaag aaaattagaa       360
ttattcacat accttagatt tgatgctgag atcactatac tcacaactgt agcagtgaat       420
ggtagtggta ataatacata cgtgggtctt cctgacttga cacttcaagc aatgtttgta       480
cccactggtg ctcttacccc agaaaagcag gactcattcc actggcagtc aggcagtaat       540
```

-continued

```
gctagtgtat tctttaaaat ctccgacccc ccagccagaa taaccatacc ttttatgtgc    600
attaactcag catactcagt ttttatgat ggctttgccg gatttgagaa aaacggtctg     660
tatggaataa atccagctga cactattggt aacttatgtg ttagaatagt gaatgaacac    720
caaccagttg gtttcacagt gaccgttagg gtttacatga agcctaaaca cataaaagca    780
tgggcaccac gaccaccacg aactctgcca tatatgagta ttgcaaatgc aaattacaaa    840
ggtaaagaaa gagcaccaaa tgcgctcagt gctataattg gcaatagaga cagtgtcaaa    900
accatgcctc ataatatagt gaacact                                        927
```

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Gln Thr Arg Thr Val Ile Asn Gln His
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Val Ala Val Asn Gly Ser Ser Asn Asn Thr
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Asp Lys Asn Phe Phe Lys Trp Thr
1               5

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 8
gtattattac cactaccatt cactgctac                                       29

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 9
gtgctgttgt tgctacctac tgccac                                          26